United States Patent
Scaria

(10) Patent No.: US 7,307,068 B2
(45) Date of Patent: *Dec. 11, 2007

(54) USE OF RAPAMYCIN TO INHIBIT IMMUNE RESPONSE AND INDUCE TOLERANCE TO GENE THERAPY VECTOR AND ENCODED TRANSGENE PRODUCTS

(75) Inventor: Abraham Scaria, Framingham, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/312,299

(22) Filed: Dec. 20, 2005

(65) Prior Publication Data

US 2006/0094684 A1    May 4, 2006

Related U.S. Application Data

(63) Continuation of application No. 10/135,164, filed on Apr. 30, 2002, which is a continuation of application No. 09/911,782, filed on Jul. 24, 2001, now abandoned, which is a continuation-in-part of application No. 09/876,574, filed on Jun. 7, 2001, now abandoned.

(60) Provisional application No. 60/221,738, filed on Jul. 31, 2000.

(51) Int. Cl.
*A61K 48/00* (2006.01)

(52) U.S. Cl. ..................... 514/44; 435/320.1

(58) Field of Classification Search ............ None
See application file for complete search history.

(56) References Cited

FOREIGN PATENT DOCUMENTS

| WO | WO 96/12406 | 5/1996 |
|----|-------------|--------|
| WO | WO 97/39776 | 10/1997 |
| WO | WO 00/63369 | 10/2000 |

OTHER PUBLICATIONS

Verma, 1997, Science, vol. 389, p. 239-242.*
Nishikawa et al. (2001, Human Gene Therapy, vol. 12, pp. 861-870).*
Anderson (1998, Nature, vol. 392, pp. 25-30).*
PCT Search Report, Jul. 25, 2001, Genzyme.
Dai, Yifan et al., Cellular and Humoral Immune Responses to Adenoviral Vectors Containing Factor IX Gene: Tolerization of Factor IX and Vector Antigens Allows for Long-Term Expression, Proc. Natl. Acad. Sci. USA, vol. 92, pp. 1401-1405, Feb. 1995, Medical Sciences.
Engelhardt, John F., Ablation of E2A in Recombinant Adenoviruses Improves Transgene Persistence and Decreases Inflammatory Response in Mouse Liver, Proc. Natl. Acad. Sci. USA, vol. 91, pp. 6196-6200, Jun. 1994, Medical Sciences.
Ilan, Yaron et al., Transient Immunosuppression With FK506 Permits Long-Term Expression of Therapeutic Genes Introduced Into the Liver Using Recombinant Adenoviruses in the Rat, Hepatology, pp. 949-956, 26(4), 1997, Chemical Abstracts Service, Columbus, Ohio.
Jenkins, Marc K., The Ups and Downs of T Cell Costimulation, Immunity, vol. 1, pp. 443-446, Sep. 1994, Cell Press.
Kay, Mark A. et al., Long-Term Hepatic Adenovirus-Mediated Gene Expression in Mice Following CTLA4Ig Administration, Nature Genetics, vol. 11, Oct. 1995, pp. 191-197.
Lenschow, Deborah J. et al., CD28/B7 System of T Cell Costimulation, Ann. Rev. Immunol., vol. 14, pp. 233-258 (1996).
Shen, Wei-Young et al., Combined Effect of Cyclosporine and Sirolimus on Improving the Longevity of Recombinant Adenovirus-Mediated Transgene Expression in the Retina, Arch Ophthalmol., vol. 119, Jul. 2001, pp. 1033-1043; American Medical Association.
Ziegler, Robin J. et al., Correction of Enzymatic and Lysosomal Storage Defects in Fabry Mice by Adenovirus-Mediated Gene Transfer, Human Gene Therapy, vol. 10, pp. 1667-1682 (Jul. 1, 1999); Mary Ann Liebert, Inc.

* cited by examiner

*Primary Examiner*—Celine Qian

(57) ABSTRACT

Disclosed are methods for transient co-administration of rapamycin together with a gene therapy vector encoding a transgene. The present invention is directed to inhibiting the immune response of a host to the administered gene therapy vector and encoded trans gene product, thus allowing persistent trans gene expression and repeated administration of the gene therapy product to the host. The present invention is also of relevance in genetic disease patients that mount immune responses to protein replacement therapies in which case the present invention provides for transient co-administration of rapamycin together with protein replacement therapy. In a further aspect of the invention, co-administration of rapamycin could inhibit a secondary immune response in a host that has been pre-immunized with the gene therapy vector or pre-immunized with the protein product encoded by the transgene.

5 Claims, 5 Drawing Sheets

USE OF RAPAMYCIN TO INHIBIT IMMUNE RESPONSE AND INDUCE TOLERANCE TO GENE THERAPY VECTOR AND ENCODED TRANSGENE PRODUCTS

The present application is a continuation of U.S. Ser. No. 10/135,164 filed Apr. 30, 2002, which is a continuation of U.S. Ser. No. 09/911,782 filed on Jul. 24, 2001 now abandoned which is a continuation in part of U.S. Ser. No. 09/876,574 filed on Jun. 7, 2001 now abandoned which claims priority to U.S. Provisional Application No. 60/221,738, filed Jul. 31, 2000. The contents of the above-referenced applications are hereby incorporated by reference into the present disclosure.

BACKGROUND

Immunosuppressant drugs have been used for purposes of preventing adverse immune responses, either a rejection of a transplanted organ, or an attack on the patients own body by its own immune system caused by an autoimmune disease, without unduly suppressing the ability of the patient's immune system to combat infection. Such immunosuppressants have included rapamycin [U.S. Pat. No. 5,694,950]; FK 506 [U.S. Pat. No. 5,365,948]; and cyclosporine.

With the advent of gene therapy, a need exists for methods of repeat administration of gene therapy vectors, such as viral vectors, exists. Methods are needed which are able to effectively overcome the body's normal immune response to gene therapy vectors such as viral vectors. In order to overcome the immunologic problems associated with repeat administration of adenoviral vectors, the use of broad immunosuppressants (Engelhardt et al., Proc. Natl. Acad. Sci. USA 91:6196-6200 (1994)) and cytoablative agents (Dai et al., Proc. Natl. Acad. Sci. USA 92:1401-1405 (1995)) to overcome the immune response of the host to first generation Ad vectors have been tested. Transient co-administration of an immunoglobulin, CTLA4-Ig, along with an intravenous injection of Ad vector expressing a non-immunogenic transgene product (human oc-I anti-trypsin) has been shown to lead to persistent transgene expression from mouse liver (Kay et al., Nat. Genetics 11:191-197 (1995)). CTLA4-Ig blocks the B7-CD28 pathway of T cell co-stimulation, which is required for optional activation of T cells. (Jenkins et al., Immunity 1:443-446 (1994); Lenschow et al., Ann. Rev. Immunol. 14:233-258 (1996)). Although adenoviral-specific antibody levels were reduced in CTLA4-Ig treated mice, the inhibition was not sufficient to allow secondary gene transfer via repeat administration of the vector under the conditions tested (Kay et al., Nat. Genetics 11:191-197 (1995)). Thus, many immunosuppressant molecules are not effective for gene therapy purposes in which persistent expression of a foreign transgene is desired. Accordingly, a need exists for methods of employing immunosuppressant drugs which are effective when used with gene therapy vectors.

SUMMARY OF INVENTION

The present invention provides for transient co-administration of rapamycin together with a gene therapy vector encoding a transgene. The present invention is directed to inhibiting the immune response of a host to the administered gene therapy vector and to the encoded transgene product, thus allowing persistent transgene expression and repeated administration of the gene therapy product to the host. The present invention is also of relevance in genetic disease patients that mount immune responses to protein replacement therapies, in which case the present invention provides for transient co-administration of rapamycin together with protein replacement therapy. In a further aspect of the invention, co-administration of rapamycin could inhibit a secondary immune response in a host that has been pre-immunized with the gene therapy vector or pre-immunized with the protein product encoded by the trans gene. In preferred embodiments, the present invention relates to methods and compositions for blocking signal 2, but not signal 1, of the interaction between major histocompatibility complex [MHC] on antigen presenting cells [APC] binding to T-cell receptor [TCR], while at the same time blocking one or more of the co-stimulation pathways: B7-CD28 and CD40-CD40 ligand. Thus, compositions of the present invention comprise (1) an agent which blocks signal 2, but not signal I, of the MHCTCR interaction pathway; (2) an agent which blocks a co-stimulation pathway; and (3) a therapeutic agent. The agent which blocks signal 2, but not signal 1, of the MHC-TCR interaction is preferably rapamycin, but may also be a rapamycin analog, an antibody which binds to the MHC, blocking interaction with TCR, or an antibody to TCR, provided such antibody to TCR is antagonistic, and does not activate the T cell to which it binds. The agent which blocks a co-stimulation pathway is preferably selected from the group consisting of CTLA4-Ig, antibodies to B7-1, antibodies to B7-2, antibodies to CD28, and antibodies to CD40L. One antibody to CD40L which may be used in the present invention as the agent blocking co-stimulation is MR1. The therapeutic agent is preferably a gene therapy vector which encodes a therapeutic gene. Suitable gene therapy vectors include viral vectors, such as adenovirus, adeno-associated virus, retrovirus, including lentivirus vectors. Other gene therapy vectors include cationic or amphiphilic compounds, such as lipids, as well as polymers, liposomes and naked DNA. Useful therapeutic genes include those encoding lysosomal storage enzymes, such as glucocerebrosidase, alpha-galactosidase A, sphingomyelinase, iduronate sulfatase, alpha-glucosidase, galactosamine-6-sulfatase, beta-galactosidase, galactosamine-4 sulfatase (arylsulfatase B), alpha-glucosidase, and alpha-iduronidase. Other preferred therapeutic genes include those useful for the production of hemophilic proteins, most preferably Factor VIIA, Factor VII and Factor IX. In other embodiments, the therapeutic agent may be a polypeptide, or a combination of polypeptide and gene therapy vectors.

DETAILED DESCRIPTION OF THE INVENTION

Figure 1:
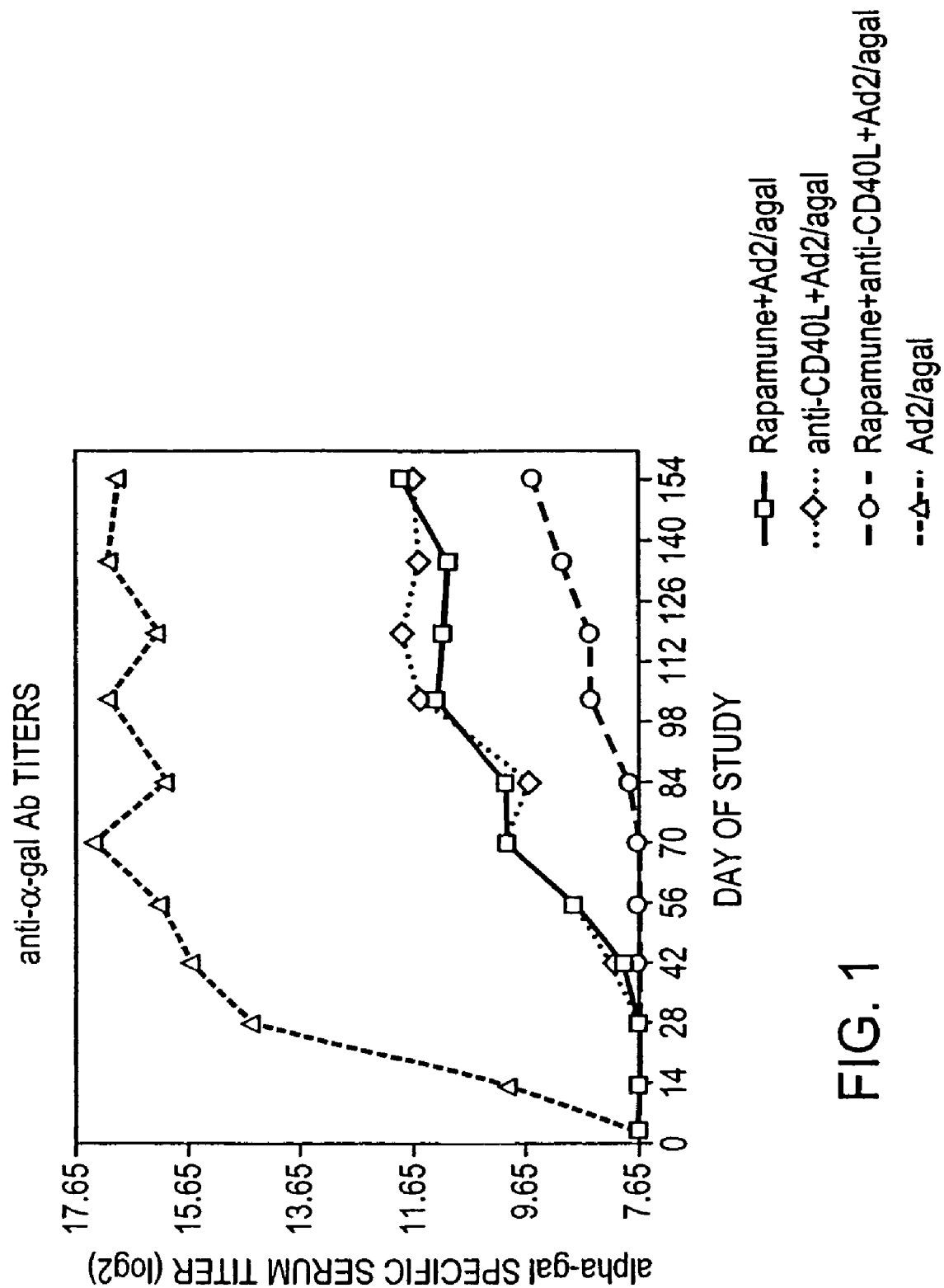
FIG. 1 shows the anti-α-gal antibody titers for experiments in which Ad2 was co-administered with anti-CD40L and/or Rapamycin.

Rapamycin is a natural product derived from a soil microorganism, which was originally described as an antibiotic and subsequently found to possess some immunosuppressive properties. Rapamycin has recently been approved for use in patients for kidney transplantation in combination with cyclosporine and corticosteroids. Recent reports in the literature claim that rapamycin in combination with co-stimulation blockade can induce tolerance to allografts in mice.

The present invention provides for transient co-administration of rapamycin or an analog or derivative thereof, together with a gene therapy vector encoding a transgene. The present invention is directed to inhibiting the immune response of a host to the administered gene therapy vector and encoded trans gene product, thus allowing persistent transgene expression and repeated administration of the gene therapy product to the host. The present invention is also of relevance in genetic disease patients that mount immune responses to protein replacement therapies in which case the present invention provides for transient co-administration of rapamycin together with protein replacement therapy. In a further aspect of the invention, co-administration of rapamycin could inhibit a secondary immune response in a host that has been pre-immunized with the gene therapy vector or pre-immunized with the protein product encoded by the transgene.

Wherever the present application refers to "rapamycin", in addition to naturally occurring forms of rapamycin, the present invention includes the use of rapamycin analogs and derivatives. Many such analogs and derivatives are known in the art, for example, including but not limited to those described in U.S. Pat. Nos. 6,015,809; 6,004,973; 5,985,890; 5,955,457; 5,922,730; 5,912,253; 5,780,462; 5,665,772; 5,637,590; 5,567,709; 5,563,145; 5,559,122; 5,559,120; 5,559,119; 5,559,112; 5,550,133; 5,541,192; 5,541,191; 5,532,355; 5,530,121; 5,530,007; 5,525,610; 5,521,194; 5,519,031; 5,516,780; 5,508,399; 5,508,290; 5,508,286; 5,508,285; 5,504,291; 5,504,204; 5,491,231; 5,489,680; 5,489,595; 5,488,054; 5,486,524; 5,486,523; 5,486,522; 5,484,791; 5,484,790; 5,480,989; 5,480,988; 5,463,048; 5,446,048; 5,434,260; 5,411,967; 5,391,730; 5,389,639; 5,385,910; 5,385,909; 5,385,908; 5,378,836; 5,378,696; 5,373,014; 5,362,718; 5,358,944; 5,346,893; 5,344,833; 5,302,584; 5,262,424; 5,262,423; 5,260,300; 5,260,299; 5,233,036; 5,221,740; 5,221,670; 5,202,332; 5,194,447; 5,177,203; 5,169,851; 5,164,399; 5,162,333; 5,151,413; 5,138,051; 5,130,307; 5,120,842; 5,120,727; 5,120,726; 5,120,725; 5,118,678; 5,118,677; 5,100,883; 5,023,264; 5,023,263; 5,023,262; all of which are incorporated herein by reference.

In the sections which follow, detailed therapeutic regimens are provided for combination therapy of eight specific LSDs (i.e. Gaucher's, Fabry's, Niemann-Pick B, Hunter's, Morquio's, Maroteaux-Lamy, Pompe's, and Hurler's-Scheie's in its various clinical manifestations), as well as hemophilic factors Factor VIIA, Factor VIII and Factor IX.

1. Gaucher's

Gaucher's disease is caused by inactivation of glucocerebrosidase and accumulation of glucocerebroside.

2. Fabry's

Fabry's disease is caused by inactivation of alpha-galactosidase A and accumulation of GL-3. The enzymatic defect leads to systemic deposition of glycosphingolipids with terminal alpha-galactosyl moieties, predominantly globotriaosylceramide and, to a lesser extent, galabiosylceramide and blood group B substances. In addition to assay for specific activity of alpha-galactosidase A and accumulation of GL-3, assay for deposition of glycosphingolipid substrates in body fluids and in lysosomes of vascular endothelial, perithelial and smooth muscle cells of blood vessels. Other manifestations which can be useful for assay include proteinuria and other signs of renal impairment, such as red cells or lipid globules in the urine, and elevated erythrocyte sedimentation rate. Also, anemia, decreased serum iron concentration, high concentration of beta-thromboglobulin, and elevated reticulocyte counts or platelet aggregation. Desnick et al., in Scriver et al., Metabolic and Molecular Bases of Inherited Disease, (7th ed. 1995) p. 2741-2784.

3. Niemann-Pick B

Niemann-Pick B disease is caused by inactivation of sphingomyelinase and accumulation of sphingomyelin.

4. Hunter's

Hunter's disease (a.k.a. MPSII) is caused by inactivation of iduronate sulfatase and accumulation of dermatan sulfate and heparan sulfate. Hunter's disease presents clinically in severe and mild forms.

5. Morquio's

Morquio's syndrome (a.k.a. MPS IV) results from accumulation of keratan sulfate due to inactivation of either of two enzymes. In MPS IVA the inactivated enzyme is galactosamine-'6sulfatase and in MPS IVB the inactivated enzyme is beta-galactosidase.

6. Maroteaux-Lamy

Maroteaux-Lamy syndrome (a.k.a. MPS VI) is caused by inactivation of galactosamine4-sulfatase (arylsulfatase B) and accumulation of dermatan sulfate.

7. Pompe's

Pompe's disease is caused by inactivation of alpha-glucosidase and accumulation of glycogen. Hers first proposed the concept of inborn lysosomal disease based on his studies of type II glycogen storage disease (a.k.a. Pompe's disease, GAA or acid maltase deficiency (AMD); see H. G. Hers, 1965, Gastroenterology 48, 625). An assay for accumulated intra lysosomal accumulation of glycogen granules, particularly in myocardium, liver and muscle fibers, or serum elevation of CK is described in Hirschorn, in Scriver et al., Metabolic and Molecular Bases of Inherited Disease, ($7^{th}$ ed. 1995) p. 2443-2464.

8. Hurler's-Scheie's

Hurler's-Scheie's disease, also known as MPS 1, is caused by inactivation of alpha-iduronidase and accumulation of dermatan sulfate and heparin sulfates, In addition to enzyme assay or by accumulation of the dermatan and heparan sulfates, assay for the disease can be by excessive urinary dermatan and heparan sulfate excretion. Nuefeld and Muenzer, in Scriver et al., Metabolic and Molecular Bases of Inherited Disease, (7th ed. 1995) p. 2465-2494.

9. Hemophilic Factors

Other preferred transgenes included genes encoding Factor VIIA, Factor VII or Factor IX. The Factor VIII gene may be full-length (see, e.g., U.S. Pat. No. 4,965,199; U.S. Pat. No. 5,618,789); B-domain deleted (see, e.g., U.S. Pat. No. 4,868,112 and U.S. Pat. No. 5,661,008) or a chimeric hybrid (see, e.g., U.S. Pat. No. 5,563,045; U.S. Pat. No. 5,888,974 and U.S. Pat. No. 5,859,204). The Factor IX gene is preferably of human origin (see, e.g., U.S. Pat. No. 4,994,371 and U.S. Pat. No. 5,521,070). The Factor VIIA gene is preferably of human origin (see, e.g., U.S. Pat. No. 4,456,591; U.S. Pat. No. 4,784,950; U.S. Pat. No. 5,190,919; U.S. Pat. No. 5,254,672 and U.S. Pat. No. 6,039,944).

Other preferred transgenes include full length cystic fibrosis transmembrane receptor (CFTR), dystrophin, ornithine transcarbamylase (OTC), alpha.1I-antitrypsin (A1AT), Rb, and p53.

Adenoviral vectors are attractive vehicles for gene transfer to a wide variety of dividing and non-dividing cells in vivo, including liver, muscle, lung, brain, heart, etc. However, transgene expression is usually transient in nature due to the generation of cellular and humoral immune responses to both Ad vector proteins and transgene products. The immune response to adenoviral vector, encoded proteins can be reduced or circumvented by using deleted partially adenoviral vectors or pseudoadenoviral vectors (PAV) that are completely deleted of adenoviral genes (also referred to as fully deleted Ad vectors, mini-adenoviral vectors, helper dependent Ad vectors or gutless Ad vectors). However, the problem remains of neutralizing antibodies to Ad capsid proteins that prevent re-administration of Ad vector of the same serotype. Adenoviral vectors, such as pseudoadenoviral vectors, retroviral vectors, adeno associate virus (AAV) vectors or lentiviral vectors do not encode any viral proteins, however, this does not address the issue of immunogenicity of the trans gene product, which could potentially be a neo-antigen in patients with genetic disease that we wish to treat with these vectors.

Viral Vectors

One of the most frequently used methods of administration of gene therapy, both in vivo and ex vivo, is the use of viral vectors for delivery of the gene. Many species of virus are known, and many have been studied for gene therapy purposes. The most commonly used viral vectors include those derived from adenoviruses, adeno-associated viruses [AAV) and retroviruses, including lentiviruses, such as human immunodeficiency virus [HIV].

Adenovirus

Adenoviral vectors for use to deliver transgenes to cells for applications such as in vivo gene therapy and in vitro study and/or production of the products of trans genes, commonly are derived from adenoviruses by deletion of the early region 1 (E1) genes (Berkner, K. L., Curro Top. Micro. Immunol. 158:39-66, 1992). Deletion of E1 genes renders such adenoviral vectors replication defective and significantly reduces expression of the remaining viral genes present within the vector. However, it is believed that the presence of the remaining viral genes in adenoviral vectors can be deleterious to the transfected cell for one or more of the following reasons: (1) stimulation of a cellular immune response directed against expressed viral proteins, (2) cytotoxicity of expressed viral proteins, and (3) replication of the vector genome leading to cell death.

One solution to this problem has been the creation of adenoviral vectors with deletions of various adenoviral gene sequences. In particular, partially deleted adenoviral vectors ["DeAd" vectors), and pseudoadenoviral vectors (PAVs), also known as 'gutless adenovirus' or mini adenoviral vectors, are adenoviral vectors derived from the genome of an adenovirus that contain minimal cis-acting nucleotide sequences required for the replication and packaging of the vector genome and which can contain one or more transgenes (See, U.S. Pat. No. 5,882,877 which covers pseudoadenoviral vectors (PAV) and methods for producing P A V, incorporated herein by reference). Such PAVs or DeAd vectors, which can accommodate up to about 36 kb of foreign nucleic acid, are advantageous because the carrying capacity of the vector is optimized, while the potential for host immune responses to the vector or the generation of replication-competent viruses is reduced. P A V and DeAd vectors contain the 5' inverted terminal repeat (ITR) and the 3' ITR nucleotide sequences that contain the origin of replication, and the cis-acting nucleotide sequence required for packaging of the adenoviral genome, and can accommodate one or more trans genes with appropriate regulatory elements, e.g. promoters, enhancers, etc.

Other adenoviral vectors have been created with the deletion of certain specific genes, which may be some or all of the adenoviral early genes, including E1, E2a, E2b [terminal peptide and DNA polymerase], E3, most or all of the E4 genes, and may also include some or all of the adenoviral late genes, L1 through L5.

Adenoviral vectors, such as DeAd vectors and PAVs, have been designed to take advantage of the desirable features of adenovirus which render it a suitable vehicle for delivery of nucleic acids to recipient cells. Adenovirus is a non-enveloped, nuclear DNA virus with a genome of about 36 kb, which has been well-characterized through studies in classical genetics and molecular biology (Hurwitz, M.S., Adenoviruses Virology, 3rd edition, Fields et al., eds., Raven Press, New York, 1996; Hitt, M. M. et al., Adenovirus Vectors, The Development of Human Gene Therapy, Friedman, T. ed., Cold Spring Harbor Laboratory Press, New York, 1999). The viral genes are classified into early (designated E1-E4) and late (designated L1-L5) transcriptional units, referring to the generation of two temporal classes of viral proteins. The demarcation of these events is viral DNA replication. The human adenoviruses are divided into numerous serotypes (approximately 47, numbered accordingly and classified into 6 groups: A, B, C, D, E and F), based upon properties including hemaglutination of red blood cells, oncogenicity, DNA and protein amino acid compositions and homologies, and antigenic relationships.

Recombinant adenoviral vectors have several advantages for use as gene delivery vehicles, including tropism for both dividing and non-dividing cells, minimal pathogenic potential, ability to replicate to high titer for preparation of vector stocks, and the potential to carry large inserts (Berkner, K. L., Curr. Top. Micro. Immunol. 158:39-66, 1992; Jolly, D., Cancer Gene Therapy 1:51-64, 1994).

PAVs and DeAd vectors have been designed to take advantage of the desirable features of adenovirus which render it a suitable vehicle for gene delivery. While adenoviral vectors can generally carry inserts of up to 8 kb in size by the deletion of regions which are dispensable for viral growth, maximal carrying capacity can be achieved with the use of adenoviral vectors containing deletions of most viral coding sequences, including PAVs. See U.S. Pat. No. 5,882,877 of Gregory et al.; Kochanek et al., Proc. Natl. Acad. Sci. USA 93:5731-5736, 1996; Parks et al., Proc. Nat!. Acad. Sci. USA 93:13565-13570, 1996; Lieber et al., J. Virol. 70:89448960, 1996; Fisher et al., Virology 217:11-22, 1996; U.S. Pat. No. 5,670,488; PCT Publication No. WO 96/33280, published Oct. 24, 1996; PCT Publication No. WO 96/40955, published Dec. 19, 1996; PCT Publication No. WO 97/25446, published Jul. 19, 1997; PCT Publication No. WO 95/29993, published Nov. 9, 1995; PCT Publication No. WO 97/00326, published Jan. 3, 1997; Morral et al., Hum. Gene Ther. 10:2709-2716, 1998.

Since P A V s and DeAd vectors are deleted for part or most of the adenovirus genome, production of PAVs requires the furnishing of adenovirus proteins in trans which facilitate the replication and packaging of a PAV genome into viral vector particles. Most commonly, such proteins are provided by infecting a producer cell with a helper adenovirus containing the genes encoding such proteins. However, such helper viruses are potential sources of contamination of a PAV or DeAd virus stock during purification and can pose potential problems when administering the adenovirus to an individual if the contaminating helper adenovirus can replicate and be packaged into viral particles.

It may be advantageous to increase the purity of a PAV or DeAd virus stock by reducing or eliminating any production of helper vectors which can contaminate preparation. Several strategies to reduce the production of helper vectors in the preparation of a DeAd virus or P A V stock are disclosed in U.S. Pat. No. 5,882,877, issued Mar. 16, 1999; U.S. Pat. No. 5,670,488, issued Sep. 23, 1997 and International Patent Application No. PCT/US99/03483, incorporated herein by reference. For example, the helper vector may contain mutations in the packaging sequence of its genome to prevent its packaging, an oversized adenoviral genome which cannot be packaged due to size constraints of the virion, or a packaging signal region with binding sequences that prevent access by packaging proteins to this signal which thereby prevents production of the helper virus.

Other strategies include the design of a helper virus with a packaging signal flanked by the excision target site of a recombinase, such as the Cre-Lox system (Parks et al., Proc. Natl. Acad. Sci. USA 93:13565-13570, 1996; Hardy et al., J. Virol. 71:1842-1849, 1997, incorporated herein by reference). Such helper vectors reduce the yield of wild-type levels.

Another hurdle for DeAd virus or PAV manufacturing, aside from the problems with obtaining helper vector-free stocks, is that the production process is initiated by DNA transfections of the DeAd virus or PAV genome and the helper genome into a suitable cell line, e.g., 293 cells. After cytopathic effects are observed in the culture indicating a successful infection, which may take up to from 2 to 6 days, the culture is harvested and is passaged onto a new culture of cells. This process is repeated for several additional passages, up to 7 times more, to obtain a modest cell lysate containing the PAV or DeAd vector and any contaminating helper vector. See Parks et al., 1996, Proc. Natl. Acad. Sci. USA 93:13565-13570; Kochanek et al., 1996, Proc. Natl. Acad. Sci. USA 93:5731-5736. This lengthy process is not optimal for commercial scale manufacturing. Additionally, this process facilitates recombination and rearrangement events resulting in the propagation of PAV or DeAd viral genomes with unwanted alterations. The use of adenoviruses for gene therapy is described, for example, in U.S. Pat. No. 5,882,877; US Patent, the disclosures of which are incorporated herein by reference.

Adeno-Associated Virus [AAV]

Adeno-associated virus (AAV) is a single-stranded human DNA parvovirus whose genome has a size about of 4.6 kb. The AA V genome contains two major genes: the rep gene, which codes for the rep proteins (Rep 76, Rep 68, Rep 52 and Rep 40) and the cap gene, which codes for AAV structural proteins (VP-1, VP-2 and VP-3). The rep proteins are involved in AAV replication, rescue, transcription and integration, while the cap proteins form the AAV viral particle. AAV derives its name from its dependence on an adenovirus or other helper virus (e.g., herpes virus) to supply essential gene products that allow AAV to undergo a productive infection, i.e., reproduce itself in the host cell. In the absence of helper virus, AAV integrates as a provirus into the host cell's chromosome, until it is rescued by superinfection of the host cell with a helper virus, usually adenovirus (Muzyczka, Curr. Top. Micro. Immunol. 158:97-127, 1992).

Interest in AAV as a gene transfer vector results from several unique features of its biology. At both ends of the AAV genome is a nucleotide sequence known as an inverted terminal repeat (ITR), which contains the cis-acting nucleotide sequences required for virus replication, rescue, packaging and integration. The integration function of the ITR mediated by the rep protein in trans permits the AAV genome to integrate into a cellular chromosome after infection, in the absence of helper virus. This unique property of the virus has relevance to the use of AAV in gene transfer, as it allows for a integration of a recombinant AAV containing a gene of interest into the cellular genome. Therefore, stable genetic transformation, ideal for many of the goals of gene transfer, may be achieved by use of rAAV vectors. Furthermore, the site of integration for AAV is well-established, and has been localized to chromosome 19 of humans (Kotin et al., Proc. Natl. Acad. Sci. 87:2211-2215, 1990). This predictability of integration site reduces the danger of random insertional events into the cellular genome that may activate or inactivate host genes or interrupt coding sequences, consequences that can limit the use of vectors whose integration is random, e.g., retroviruses. However, because the rep protein mediates the integration of AA V, removal of this gene in the design of rAAV vectors may result in the altered integration patterns that have been observed with rAAV vectors (Ponnazhagan et al., Hum. Gene Ther. 8:275-284, 1997).

There are other advantages to the use of AAV for gene transfer. The host range of AAV is broad. Moreover, unlike retroviruses, AAV can infect both quiescent and dividing cells. In addition, AAV has not been associated with human disease, obviating many of the concerns that have been raised with retrovirus-derived gene transfer vectors.

Standard approaches to the generation of recombinant rAAV vectors have required the coordination of a series of intracellular events: transfection of the host cell with an rAAV vector genome containing a trans gene of interest flanked by the AAV ITR sequences, transfection of the host cell by a plasmid encoding the genes for the AA V rep and cap proteins which are required in trans, and infection of the transfected cell with a helper virus to supply the non-AAV helper functions required in trans (Muzyczka, N., Curf. Top. Micro. Immunol. 158: 97-129, 1992). The adenoviral (or other helper virus) proteins activate transcription of the AAV rep gene, and the rep proteins then activate transcription of the AAV cap genes. The cap proteins then utilize the ITR sequences to package the rAAV genome into an rAAV viral particle. Therefore, the efficiency of packaging is determined, in part, by the availability of adequate amounts of the structural proteins, as well as by the accessibility of any cis-acting packaging sequences required in the rAAV vector genome.

One of the potential limitations to high level rAAV production derives from limiting quantities of the AAV helper proteins required in trans for replication and packaging of the rAAV genome. Some approaches to increasing the levels of these proteins have included placing the AAV rep gene under the control of the HIV LTR promoter to increase rep protein levels (Flotte, F. R. et al., Gene Therapy 2:29-37, 1995); the use of other heterologous promoters to increase expression of the AAV helper proteins, specifically the cap proteins (Vincent et al., J. Virol. 71:1897-1905, 1997); and the development of cell lines that specifically express the rep proteins (Yang, Q. et al., J. Virol. 68:4847-4856, 1994).

Other approaches to improving the production of rAAV vectors include the use of helper virus induction of the AAV helper proteins (Clark et al., Gene Therapy 3:1124-1132, 1996) and the generation of a cell line containing integrated copies of the rAAV vector and AAV helper genes so that infection by the helper virus initiates rAAV production (Clark et al., Human Gene Therapy 6:1329-1341, 1995).

rAAV vectors have been produced using replication-defective helper adenoviruses which contain the nucleotide sequences encoding the rAAV vector genome (U.S. Pat. No. 5,856,152 issued Jan. 5, 1999) or helper adenoviruses which contain the nucleotide sequences encoding the AAV helper proteins (PCT International Publication WO95/06743, published Mar. 9, 1995). Production strategies which combine high level expression of the AAV helper genes and the optimal choice of cis-acting nucleotide sequences in the rAAV vector genome have been described (PCT International Application No. WO97/09441 published Mar. 13, 1997).

Current approaches to reducing contamination of rAAV vector stocks by helper viruses, therefore, involve the use of temperature-sensitive helper viruses (Ensinger et al., J. Virol. 10:328-339, 1972), which are inactivated at the non-permissive temperature. Alternatively, the non-AAV helper genes can be sub cloned into DNA plasmids which are transfected into a cell during rAAV vector production (Salvetti et al., Hum. Gene Ther. 9:695-706, 1998; Grimm et al., Hum. Gene Ther. 9:2745-2760, 1998). The use of AAV for gene therapy is described, for example, in U.S. Pat. No. 5,753,500; US Patent, the disclosures of which are hereby incorporated herein by reference.

Retroviruses

Retrovirus vectors are a common tool for gene delivery (Miller, Nature (1992) 357:455460). The ability of retrovirus vectors to deliver an unrearranged, single copy gene into a broad range of rodent, primate and human somatic cells makes retroviral vectors well suited for transferring genes to a cell.

Retroviruses are RNA viruses wherein the viral genome is RNA. When a host cell is infected with a retrovirus, the genomic RNA is reverse transcribed into a DNA intermediate which is integrated very efficiently into the chromosomal DNA of infected cells. This integrated DNA intermediate is referred to as a provirus. Transcription of the provirus and assembly into infectious virus occurs in the presence of an appropriate helper virus or in a cell line containing appropriate sequences enabling encapsidation without coincident production of a contaminating helper virus. A helper virus is not required for the production of the recombinant retrovirus if the sequences for encapsidation are provided by co-transfection with appropriate vectors.

Another useful tool for producing recombinant retroviral vectors are packaging cell lines which supply in trans the proteins necessary for producing infectious virions, but those cells are incapable of packaging endogenous viral genomic nucleic acids (Watanabe & Temin, Molec. Cell. Biol. (1983) 3(12):2241-2249; Mann et al., Cell (1983) 33:153-159; Embretson & Temin, J. Viroi. (1987) 61 (9): 2675-2683). One approach to minimize the likelihood of generating RCR in packaging cells is to divide the packaging functions into two genomes, for example, one which expresses the gag and pol gene products and the other which expresses the env gene product (Bosselman et al., Molec. Cell. Biol. (1987) 7(5):1797-1806; Markowitz et al., J. Viroi. (1988) 62(4): 1120-1124; Danos & Mulligan, Proc. Natl. Acad. Sci. (1988) 85:6460-6464). That approach minimizes the ability for co-packaging and subsequent transfer of the two-genomes, as well as significantly decreasing the frequency of recombination due to the presence of three retroviral genomes in the packaging cell to produce RCR.

In the event recombinants arise, mutations (Danos & Mulligan, supra) or deletions (Boselman et al., supra; Markowitz et al., supra) can be configured within the undesired gene products to render any possible recombinants non-functional. In addition, deletion of the 3' LTR on both packaging constructs further reduces the ability to form functional recombinants.

The retroviral genome and the proviral DNA have three genes: the gag, the pol, and the env, which are flanked by two long terminal repeat (LTR) sequences. The gag gene encodes the internal structural (matrix, capsid, and nucleocapsid) proteins; the pol gene encodes the RNA-directed DNA polymerase (reverse transcriptase) and the env gene encodes viral envelope glycoproteins. The 5' and 3' LTRs serve to promote transcription and polyadenylation of the virion RNAs. The LTR contains all other cis-acting sequences necessary for viral replication. Lentiviruses have additional genes including vit vpr, tat, rev, vpu, nef, and vpx (in HIV-1, HIV-2 and/or SIV). Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the result is a cis defect which prevents encapsidation of genomic RNA. However, the resulting mutant is still capable of directing the synthesis of all virion proteins.

Lentiviruses are complex retroviruses which, in addition to the common retroviral genes gag, pol and env, contain other genes with regulatory or structural function. The higher complexity enables the lentivirus to modulate the life cycle thereof, as in the course of latent infection. A typical lentivirus is the human immunodeficiency virus (HIV, the etiologic agent of AIDS. In vivo, HIV can infect terminally differentiated cells that rarely divide, such as lymphocytes and macrophages. In vitro, HIV can infect primary cultures of monocyte-derived macrophages (MDM) as well as HeLa-Cd4 or T lymphoid cells arrested in the cell cycle by treatment with aphidicolin or gamma irradiation. Infection of cells is dependent on the active nuclear import of HIV preintegration complexes through the nuclear pores of the target cells. That occurs by the interaction of multiple, partly redundant, molecular determinants in the complex with the nuclear import machinery of the target cell. Identified determinants include a functional nuclear localization signal (NLS) in the gag matrix (MA) protein, the karyophilic virion-associated protein, vpr, and a C-terminal phosphotyrosine residue in the gag MA protein. The use of retroviruses for gene therapy is described, for example, in U.S. Pat. No. 6,013,516; and U.S. Pat. No. 5,994,136, the disclosures of which are incorporated herein by reference.

Non-Viral Vectors

Other methods for delivery of DNA to cells do not use viruses for delivery. These include the use of compounds, such as cationic amphiphilic compounds; as well as DNA in the absence of viral or non-viral compounds, known as "naked DNA."

Cationic Amphiphilic Compounds:

Because compounds designed to facilitate intracellular delivery of biologically active molecules must interact with both non-polar and polar environments (in or on, for example, the plasma membrane, tissue fluids, compartments within the cell, and the biologically active molecule itself), such compounds are designed typically to contain both polar and non-polar domains. Compounds having both such domains may be termed amphiphiles, and many lipids and synthetic lipids that have been disclosed for use in facilitating such intracellular delivery (whether for in vitro or in vivo application) meet this definition. One particularly important class of such amphiphiles is the cationic amphiphiles. In general, cationic amphiphiles have polar groups that are capable of being positively charged at or around physiological pH, and this property is understood in the art to be important in defining how the amphiphiles interact with the many types of biologically active (therapeutic) molecules including, for example, negatively charged polynucleotides such as DNA.

Examples of cationic amphiphilic compounds that have both polar and non-polar domains and that are stated to be useful in relation to intracellular delivery of biologically active molecules are found, for example, in the following references, which contain also useful discussion of (1) the properties of such compounds that are understood in the art as making them suitable for such applications, and (2) the nature of structures, as understood in the art, that are formed by complexing of such amphiphiles with therapeutic molecules intended for intracellular delivery.

(1) Feigner, et al., Proc. Natl. Acad. Sci. USA, 84,7413-7417 (1987) disclose use of positively-charged synthetic cationic lipids including N->1 (2,3-dioleyloxy) propyl!-N, N,N-trimethylammonium chloride ("DOTMA"), to form lipid/DNA complexes suitable for transfections. See also Feigner et al., The Journal of Biological Chemistry, 269(4), 2550-2561 (1994).

(2) Behr et al., Proc. Natl. Acad. Sci. USA, 86, 6982-6986 (1989) disclose numerous amphiphiles including dioctadecylamidologlycylspermine ("DOGS").

(3) U.S. Pat. No. 5,283,185 to Epand et al. describes additional classes and species of amphiphiles including 3.beta.>N-(N.sup.1,N.sup.1-dimethylaminoethane) carbamoyl! cholesterol, termed "DC-chol".

(4) Additional compounds that facilitate transport of biologically active molecules into cells are disclosed in U.S. Pat. No. 5,264,618 to Felgner et al. See also Felgner et al., The Journal Of Biological Chemistry, 269(4), pp. 2550-2561 (1994) for disclosure therein of further compounds including "DMRIE" 1,2-dimyristyloxypropyl-3-dimethyl-hydroxyethyl ammonium bromide.

(5) Reference to amphiphiles suitable for intracellular delivery of biologically active molecules is also found in U.S. Pat. No. 5,334,761 to Gebeyehu et al., and in Feigner et al., Methods (Methods in Enzymology), 5, 67-75 (1993).

The use of compositions comprising cationic amphiphilic compounds for gene delivery is described, for example, in U.S. Pat. No. 5,049,386; U.S. Pat. No. 5,279,833; U.S. Pat. No. 5,650,096; U.S. Pat. No. 5,747,471; U.S. Pat. No. 5,767,099; U.S. Pat. No. 5,910,487; U. 5,719,131; U.S. Pat. No. 5,840,710; U.S. Pat. No. 5,783,565; U.S. Pat. No. 5,925,628; U.S. Pat. No. 5,912,239; U. 5,942,634; U.S. Pat. No. 5,948,925; U.S. Pat. No. 6,022,874; U.S. Pat. No. 5,994,317; U.S. Pat. No. 5,861,397; U. 5,952,916; U.S. Pat. No. 5,948,767; U.S. Pat. No. 5,939,401; and U.S. Pat. No. 5,935,936, the disclosures of which are hereby incorporated by reference.

"Naked DNA" Transfer

Methods for delivering a non-infectious, non-integrating DNA sequence encoding a desired polypeptide or peptide operably linked to a promoter, free from association with transfection-facilitating proteins, viral particles, liposomal formulations, charged lipids and calcium phosphate precipitating agents is described in U.S. Pat. No. 5,580,859; U.S. Pat. No. 5,963,622; U.S. Pat. No. 5,910,488; the disclosures of which are hereby incorporated by reference.

Combined Viral and Non-Viral Gene Transfer Systems

Gene transfer systems that combine viral and nonviral components have been reported. Cristiano et al. (1993) Proc. Natl. Acad. Sci. USA 90: 11548; Wu et al. (1994) J. Biol. Chem. 269: 11542; Wagner et al. (1992) Proc. Natl. Acad. Sci. USA 89: 6099; Yoshimura et al., (1993) J. Biol. Chem. 268: 2300; Curiel et al. (1991) Proc. Natl. Acad. Sci USA 88: 8850; Kupfer et al. (1994) Hum. Gene Ther. 1437; and Gottschalk et al. (1994) Gene Ther. 1:185. In most cases, adenovirus has been incorporated into the gene delivery systems to take advantage of its endosomolytic properties. The reported combinations of viral and nonviral components generally involve either covalent attachment of the adenovirus to a gene delivery complex or co-internalization of unbound adenovirus with cationic lipid: DNA complexes.

In a specific example, we have co-administered rapamycin together with Ad2/α-gal vector. The rapamycin treatment (70 ug per mouse) was given by I.P. injections daily for 7 days. The Ad2/α-gal vector was delivered I.V. As seen in the figures, transient treatment with rapamycin was able to significantly inhibit CTL responses to Ad vector and Ad/α-gal vector. The antibody responses to both Ad vector and a-galactosidase protein was also significantly inhibited.

Dosage of Rapamycin

The optimal dosage of rapamycin may be derived by methods known in the clinical arts, including, but not limited to linear equations based on population parameters such as age, weight or sex; non-linear least squares modeling methods; Bayesian analysis which employs specific data about the medical status of a particular patient; pharmacokinetics compartment modeling; and the trial-and-error method, in which a patient could be given incremental dosages of rapamycin, and the patient's reaction thereto could be observed and used to determine the frequency and quantity of subsequent dosages. Preferred methods for dosing are the methods described in U.S. Pat. No. 5,694,950, the disclosure of which is hereby incorporated herein by reference. In general, a preferred dosage of rapamycin is expected to be from about 0.05 to about 0.15 milligrams of rapamycin per kilogram of the patient's body weight. This dosage may be increased in order to obtain additional efficacy.

The dosage of gene vector may be determined by one who is expert in the field. For viral gene therapy, the dosage will generally be in the preferred ranges from about 10e9 to about 10e13 particles per kg/body weight for adenovirus; from about 10e9 to about 10e14 particles per kg/body weight for AAV; and from about 10e6 to about 10e10 transducing units/kg/body weight for retrovirus or lentivirus.

Rapamycin+Anti-CD40L Experiments

Figure 2:
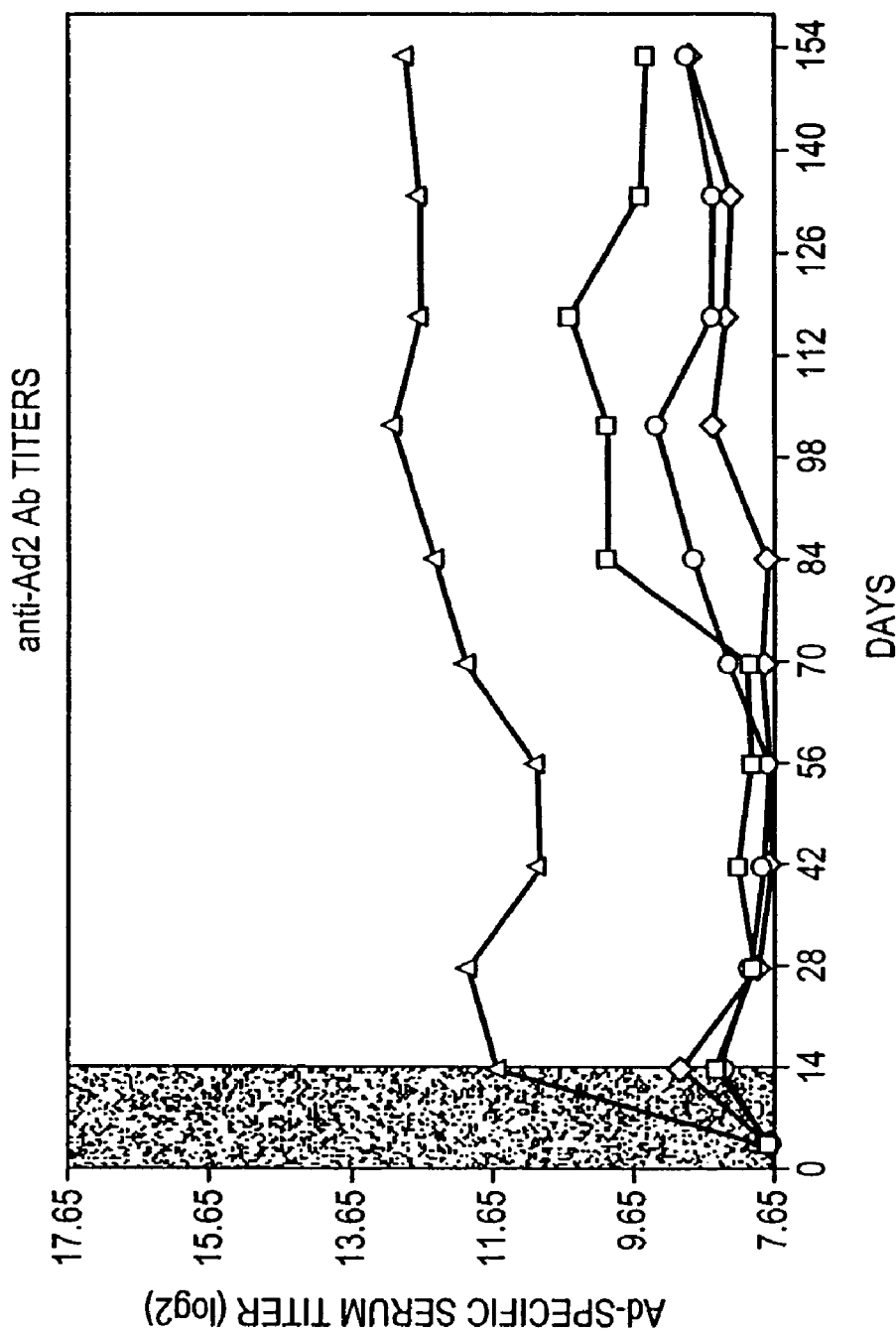
FIG. 2 shows the anti-α-Ad2 antibody titers for experiments in which Ad2 was co-administered with anti-CD40L and/or Rapamycin.
Figure 3:
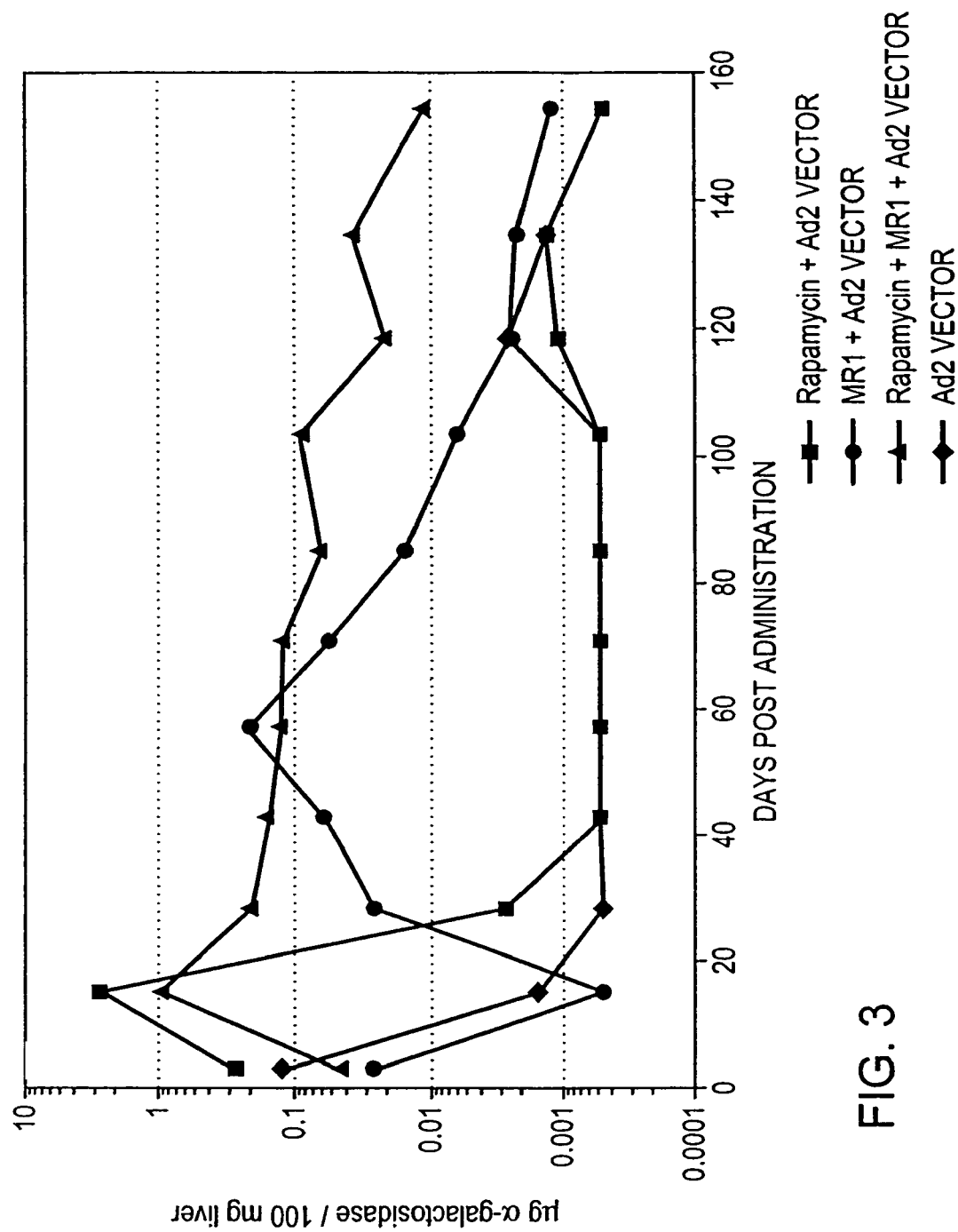
FIG. 3 shows the transgene expression for experiments in which Ad2 was co administered with anti-CD40L and/or Rapamycin.

Balb/c mice were injected intravenously with 6e10 particles/mouse of Ad2/CMVα-gal vector on day 0. Mice were given intraperitoneal injections of 500 ug/mouse of MR-1, an anti-CD40L antibody, on days −I, +2, +7 and +13. Rapamycin was injected I.P. at 2.5 mg/kg daily from day 0 to +13. One control group of mice received Ad2/CMVα-gal vector alone. Treatment groups received (1) Ad vector +Rapamycin; (2) Ad vector +anti-CD40L; or (3) Ad vector +Rapamycin +anti-CD40L. Results are shown in FIG. 1 [anti-α-gal antibody titers] and FIG. 2 [anti-Ad2 antibody titers]. All groups of mice were bled at the indicated time points to assay for antibodies to Ad2 and α-galactosidase protein expression levels in the serum. As can be seen from the results, anti-α-gal antibody and anti-Ad2 antibody titers were significantly lower in the treatment groups than in the control group. As seen in FIG. 3, transient treatment with anti-CD40L and Rapamycin led to persistent transgene expression for periods as long as 160 days.

Rapamycin+Anti-B7 Experiments

Figure 4:
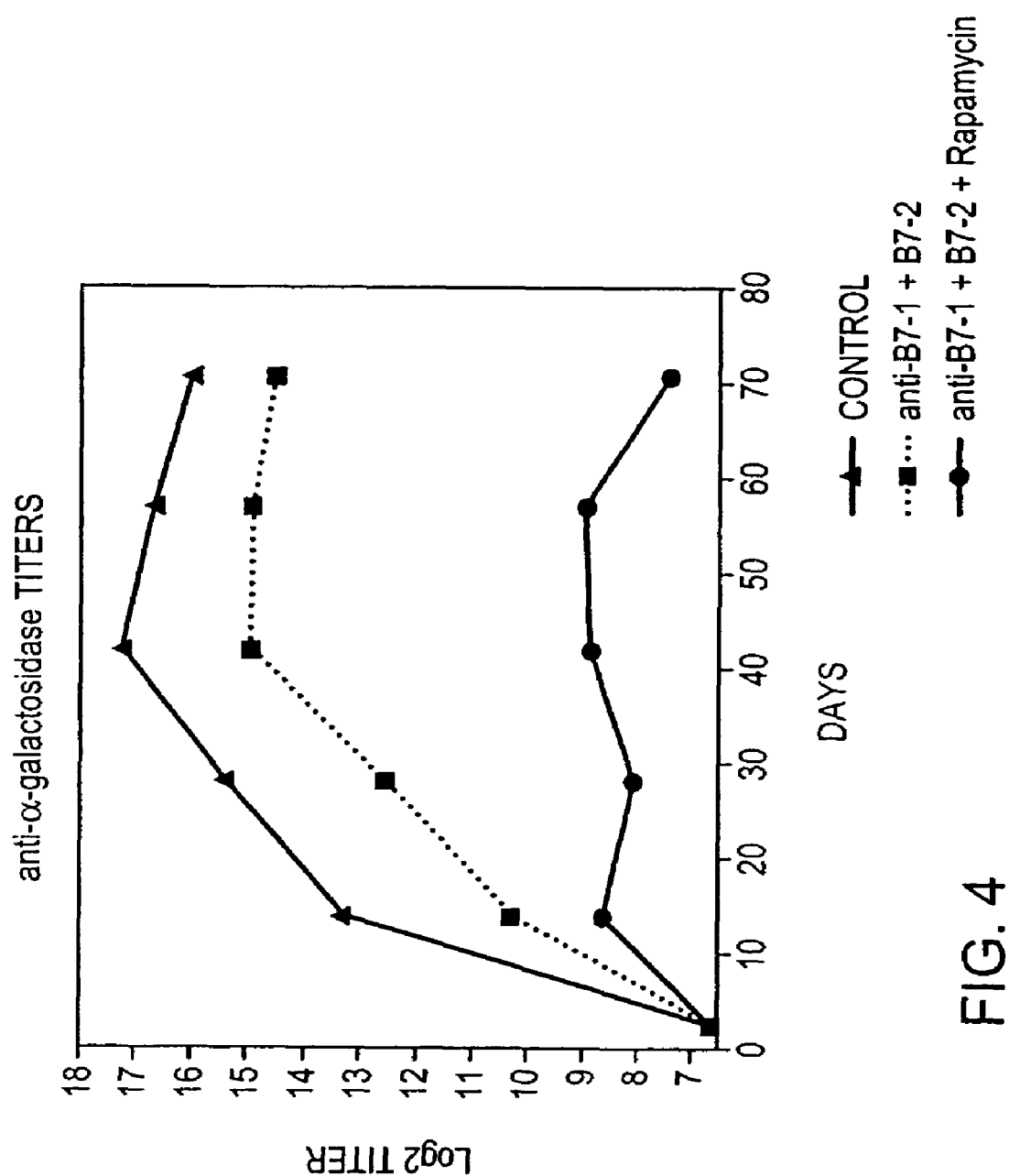
FIG. 4 shows the anti-α-gal antibody titers for experiments in which Ad2 was co-administered with anti-B7-1 and anti-B7-2 and/or Rapamycin.
Figure 5:
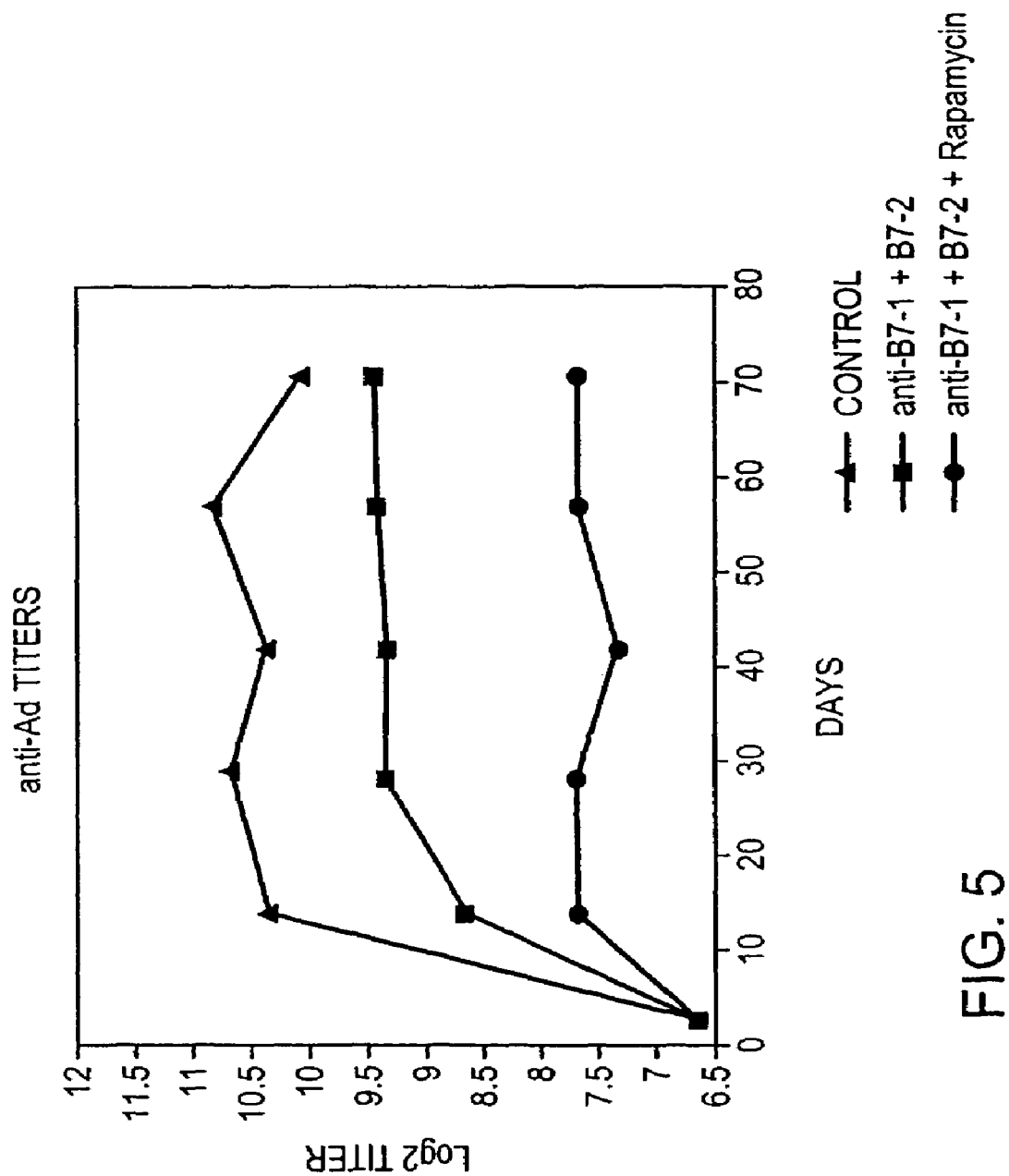
FIG. 5 shows the anti-α-Ad2 antibody titers for experiments in which Ad2 was co-administered with anti-B7-1 and anti-B7-2 and/or Rapamycin.

Balb/c mice were injected intravenously with 7e10 particles/mouse of Ad2/CMVHIα-gal vector on day 0. Mice were given intraperitoneal injections of 100 ug/mouse of anti-B7-1, and 100 ug/mouse of anti-B7-2 on days −I, +2 and +7. Rapamycin was injected I.P. at 2.5 mg/kg daily from day 0 to +13. One control group of mice received Ad2/CMVHIα-gal vector alone. Treatment groups received (1) Ad vector +anti-B7-1+anti-B7-2; or (2) Ad vector +anti-B7-1+anti-B7-2+Rapamycin. Results are shown in FIG. 3 [anti-α-gal antibody] and FIG. 4 [anti-Ad2 antibody titers]. All groups of mice were bled at the indicated time points to assay for antibodies to Ad2 and α-galactosidase protein expression levels in the serum. As can be seen from the results, anti-α-gal antibody and anti-Ad2 antibody titers were significantly lower in the treatment groups than in the control group.

The above examples are non-limiting, and are included for illustrative purposes only. The skilled artisan, having read the disclosure contained herein, will readily appreciate that many modifications, additions and improvements are possible. Such modifications, additions and improvements are part of the present invention.

The disclosure of each and every publication mentioned in this specification is hereby incorporated by reference for the teachings contained therein.

I claim:

1. A method for inhibiting the immune response of a host to an adeno-associated virus gene therapy vector comprising a transgene encoding a protein of interest, said method comprising:
   1) co-administering the gene therapy vector with an effective amount of rapamycin to said host, wherein the humoral immune response to the adeno-associated virus gene therapy vector of the rapamycin-treated host is reduced as compared to a host treated with the vector alone.

2. The method of claim 1, wherein the method further comprises administering an effective amount of an agent which blocks a co-stimulation pathway.

3. The method of claim 2, wherein the agent which blocks a co-stimulation pathway is selected from the group consisting of CTLA4-Ig, antibodies to B7-1, antibodies to B7-2, antibodies to CD28, antibodies to CD40L; and combinations of the above.

4. The method of claim 3, wherein the transgene encodes a protein selected from the group consisting of glucocerebrosidase, alpha-galactosidase A, beta-galactosidase, sphingomyelinase, iduronate sulfatase, alpha-glucosidase and alpha-iduronidase.

5. The method of claim 3, wherein the transgene encodes a protein selected from the group consisting of Factor VIIA, Factor VIII or Factor IX.

* * * * *